United States Patent [19]
Parrish

[11] Patent Number: 6,096,687
[45] Date of Patent: *Aug. 1, 2000

[54] HERBICIDAL COMPOSITIONS

[75] Inventor: Scott K. Parrish, Veradale, Wash.

[73] Assignee: Monsanto Company, St. Louis, Mo.

[ * ] Notice: This patent issued on a continued prosecution application filed under 37 CFR 1.53(d), and is subject to the twenty year patent term provisions of 35 U.S.C. 154(a)(2).

[21] Appl. No.: 08/860,887

[22] PCT Filed: Nov. 27, 1995

[86] PCT No.: PCT/IB95/01059

§ 371 Date: Aug. 15, 1997

§ 102(e) Date: Aug. 15, 1997

[87] PCT Pub. No.: WO96/19110

PCT Pub. Date: Jun. 27, 1996

[30] Foreign Application Priority Data

Dec. 22, 1994 [EP] European Pat. Off. .............. 94870207

[51] Int. Cl.⁷ .......................... A01N 43/52; A01N 43/54; A01N 43/78; A01N 43/00
[52] U.S. Cl. .......................... 504/130; 504/129; 504/131; 504/132; 504/133; 504/134; 504/135; 504/136; 504/137; 504/138; 504/139; 504/140; 504/141; 504/142; 504/143; 504/144; 504/145; 504/146; 504/147; 504/148
[58] Field of Search .................................... 504/129–139, 504/140–148

[56] References Cited

FOREIGN PATENT DOCUMENTS 477808  4/1992  European Pat. Off. .
98/24320  6/1998  WIPO .

*Primary Examiner*—John Pak
*Attorney, Agent, or Firm*—Howrey Simon Arnold & White LLP; Carter J. White

[57] ABSTRACT

A herbicidal composition comprising a sulfonylurea derivative of formula (I)

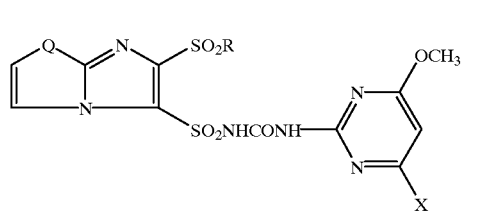

wherein Q is —CH=CH— or —S—, R is straight or branched C1–3 alkyl, and X is —OCH₃ or —CH₃, or an agriculturally acceptable salt thereof, and at least one co-herbicide selected from: urea herbicides, imidazolinone herbicides, diphenyl ether herbicides, hydroxybenzonitrile herbicides, 2-(4-aryloxyphenoxy) alkanoic acid herbicides and oxime herbicides, carbamate and thiocarbamate herbicides, quaternary ammonium salt herbicides, triazole herbicides, phytohormone herbicides, including aryloxyalkanoic acid herbicides, arenecarboxylic acid herbicides, pyridinecarboxylic acid herbicides, and pyridyloxyacetic acid herbicides, 2,6-dinitroaniline herbicides, amide herbicides, and anilide herbicides, the respective herbicidal constituents being present in amounts such that the compositions display selectivity of herbicidal action with respect to crops being treated pre- or post-emergent and exhibit synergistic effects when applied at herbicidally effective rates.

7 Claims, No Drawings

HERBICIDAL COMPOSITIONS

This application is a 371 of PCT/IB95/01059, filed on Nov. 27, 1995.

This invention relates to herbicidal compositions comprising a herbicidal sulfonylurea derivative and at least one co-herbicide selected from a range of co-herbicides. It further relates to the use of the aforesaid herbicidal compositions for controlling undesired vegetation in crops, especially cereal crops.

EP-A-0 477 808 discloses sulfonylurea derivatives of the general formula (I)

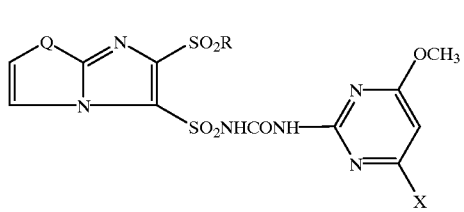

wherein Q is —CH=CH— or —S—, R is straight or branched C1–3 alkyl, and X is —OCH$_3$ or CH$_3$, or an agriculturally acceptable salt thereof. Examples of agriculturally acceptable salts include salts with inorganic bases such as alkali metal (e.g. sodium, potassium, etc.), alkali earth metal (e.g. magnesium, calcium, etc.) and ammonia as well as organic bases such as dimethylamine, triethylamine, pyrrolidine, piperidine, piperazine, morpholine, benzylamine, ethanolamine, and diethanolamine. The said herbicidal sulfonylurea derivatives are said to present advantageous activity against broadleaf weeds and graminaceous weeds without adverse effects on valuable small grain cereal crop particularly wheat.

The aforesaid sulfonylurea derivatives do not readily control all the weed species encountered in small grain cereal crops in practice. More particularly weeds such as, for example:

*Alopecurus myosuroides* (black grass)
*Avena fatua* (wild oats)
*Galium aparine* (bedstraw cleavers)
*Lamium purpureum* (red dead nettle)
*Matricaria chamomilla* (mayweed)
*Stellaria media* (common chickweed)
*Veronica persica* (common field speedwell)

are not easily controlled by said derivatives unless relatively high rates are used. These high rates may then be detrimental to the crops and, of course, reduce the commercial value of the sulfonylurea derivatives. Moreover, environmental considerations increasingly require that lower amounts of herbicidally active substances be used in the control of undesired vegetation.

It is known to overcome this type of problem to some extent by the use of herbicidal compositions in which more than one type herbicide is present. Such compositions, however, should preferably still show the advantageous properties of the individual herbicide constituents and display a synergistic effect between them, whilst maintaining selectivity of herbicidal action with respect to the crop. It is, nonetheless, difficult to determine appropriate combinations of herbicides in view of the considerable number of different types of herbicides available and the plurality of individual herbicides within each such type.

The purpose of the present invention is to provide herbicidal compositions comprising a sulfonylurea derivative as defined above and at least one co-herbicide, said compositions having a broader spectrum of weed control than each individual herbicide constituent, whilst retaining the selectivity of herbicidal action of the sulfonylurea derivative constituent.

A further purpose of the present invention is to provide herbicidal compositions which, when applied pre-emergent or post-emergent, display an enhanced and broader spectrum of herbicidal activity than the sulfonyl urea derivatives used alone, whilst retaining the selectivity of action of the herbicidal action of the sulfonylurea derivatives defined above with regard to the crops being treated.

A further purpose of the present invention is to provide a method of controlling the germination and growth of undesired vegetation in a selective manner with regard to crops, e.g. cereal crops, being treated, which comprises applying to the crop, pre- or post-emergent, a composition according to the present invention.

It is surprising that the compositions of the present invention comprising a sulfonylurea herbicide as defined and at least one co-herbicide are particularly efficient in combating a broad spectrum of weeds while still displaying a selectivity of action with respect to the crops. It is further surprising that the compositions of the present invention additionally exhibit synergistic effects.

According to the present invention there are provided herbicidal compositions comprising a sulfonylurea derivative of formula (I) as defined above and at least one co-herbicide selected from:

urea herbicides,
imidazolinone herbicides,
diphenyl ether herbicides,
hydroxybenzonitrile herbicides,
2-(4-aryloxyphenoxy) alkanoic acid herbicides and oxime herbicides,
carbamate and thiocarbamate herbicides,
quaternary ammonium salt herbicides,
triazole herbicides,
phytohormone herbicides, including aryloxyalkanoic acid herbicides, arenecarboxylic acid herbicides, pyridinecarboxylic acid herbicides, and
pyridyloxyacetic acid herbicides,
2,6-dinitroaniline herbicides,
amide herbicides, and
anilide herbicides, in amounts such that the compositions display selectivity of herbicidal action with respect to crops being treated pre- or post-emergent and exhibit synergistic effects when applied at herbicidally effective rates.

Thus, the ratio of the sulfonylurea herbicide to the co-herbicide is, as appropriate, i.e. depending upon the specific herbicides present in the composition according to the invention, from about 1:1 to about 1:150 and the amounts applied are in the ratio of from about 10:30 g/ha to about 25:1500 g/ha.

The above classification of co-herbicides is based upon the classification of herbicides used in "The Pesticide Manual", ninth edition, published in 1991 by the British Crop Protection Council.

It has been found that the compositions according to the present invention show improved herbicidal efficacy with respect to the sulfonylurea derivative (I) constituent on its own since they do not present the same weaknesses on weed species which are difficult to control by the use of the sulfonylurea derivative alone. Moreover, the range of weeds on which the compositions of the present invention are herbicidally effective is broadened when compared to the use of the respective sulfonylurea herbicide on its own.

Furthermore, the beneficial selectivity of action of the sulfonylurea herbicide constituent with regard to cereals (including, but not limited to, wheat, barley, oats and rye), is not adversely affected.

It is further surprising that the compositions according to the present invention do not simply present an additive herbicidal effect against most of the weeds encountered in monocotyledonous crops, but show a synergistic effect.

As a consequence, the amounts of the individual herbicidally active constituents in the compositions of the present invention which require to be applied to crops can be reduced over the quantities required when they are used alone, whilst maintaining the efficacy of the herbicidal action at the same level. In addition, the compositions even show an acceptable level of activity against weeds where each of the herbicides used individually would be inefficient on its own because the amount used would be too low, thus permitting an increase in the safety margin for sub-optimal applications.

Preferred sulfonylurea derivatives are those according to formula I above in which —R is —C$_2$H$_5$, —X is —OCH$_3$, and Q is —CH=CH— or —S—, i.e. compounds A and B (see Example 1).

Preferred urea herbicides include isoproturon, chlortoluron, metoxuron, linuron, monolinuron, dimefuron and diuron. Isoproturon is particularly preferred.

Preferred imidazolinone herbicides include imazamethabenz-methyl, imazapyr, imazaquin, and imazapyr ammonium. Imazamethabenz-methyl ("ASSERT"—trade mark) is particularly preferred.

Preferred diphenyl ether herbicides include bifenox, acifluorfen, fluoroglycofen ethyl, fomesafen, lactofen, and oxyfluorfen. Bifenox is particularly preferred.

Preferred hydroxybenzonitrile herbicides include bromoxynil and ioxynil. Bromoxynil is particularly preferred.

Preferred 2-(4-aryloxyphenoxy) alkanoic acid herbicides include fenoxaprop ethyl, fenoxaprop-P-ethyl ("PUMA"—trademark), fluazifop-P, fluazifop-butyl, haloxyfop-methyl, haloxyfop-etotyl, isoxapyrifop, propaquizafop-ethyl, quizalofop-ethyl, quizalofop-P-ethyl, and diclofop-methyl.

Preferred carbamate/thiocarbamate herbicides include tri-allate, di-allate, barban, dimepiperate, molinate, and thiobencarb. Tri-allate is particularly preferred.

A particularly preferred quaternary ammonium salt herbicide is difenzoquat metilsulfate.

A preferred triazole derivative has the following formula (II)

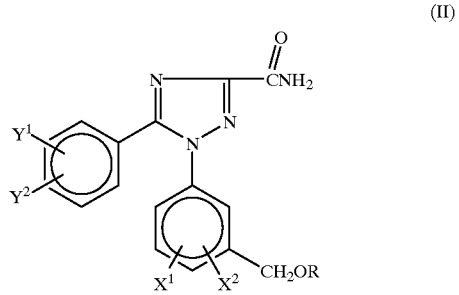

wherein R is a straight-chain alkyl group having 1 to 10 carbon atoms which is non-substituted or substituted with 1 to 19 fluorine atoms, a branched alkyl group having 3 to 10 carbon atoms which is non-substituted or substituted with 1 to 19 fluorine atoms, a cyclic alkyl group having 3 to 10 carbon atoms, an alkyl group having 1 to 3 carbon atoms which is substituted with an alicyclic structure having 3 to 7 carbon atoms, a phenyl group or an aralkyl group having 7 to 9 carbon atoms:; X$^1$ is a halogen or an alkyl group having 1 to 3 carbon atoms; X$^2$ is a hydrogen, a halogen or an alkyl group having 1 to 3 carbon atoms; Y$^1$ is a hydrogen or a fluorine; and Y$^2$ is a hydrogen or a fluorine, more preferably where X$^1$ is chlorine, X$^2$ is hydrogen, Y$^1$ and Y$^2$ are hydrogen and R means —CH$_2$CF$_2$CF$_3$. It is known to show pre-emergent and post-emergent herbicidal activity. Another preferred triazole herbicide is amitrole.

A particularly preferred triazole herbicide is flupoxam. This compound corresponds to formula II above in which Y$^1$ and Y$^2$ are hydrogen, X$^1$ is chlorine, X$^2$ is hydrogen and R is —CH$_2$CF$_2$CF$_3$.

Preferred phytohormone herbicides include the aryloxy-alkanoic acid herbicides 2,4-D, 2,4 DB, MCPA, MPCB, PCPB, MCPP (known as CMPP and mecoprop), mecoprop-P, dichlorprop, dichlorprop-P, and clomeprop, the arenecarboxylic acid herbicide dicamba, the pyridinecarboxylic acid herbicide picloram, the pyridyloxyacetic acid herbicides fluroxypyr, triclopyr-butotyl, and triclopyr-triethylammonium. Of the foregoing MCPP and fluroxypyr are particularly preferred.

Preferred 2,6-dinitroaniline herbicides include pendimethalin, trifluralin, fluazinam, benfluralin, butralin and fluchloralin. Pendimethalin is particularly preferred.

Preferred oxime herbicides include tralkoxydim, sethoxydim, alloxydim and clethodim.

Preferred amide herbicides include isoxaben, tebutam, and propyzamide. Isoxaben is particularly preferred.

Preferred anilide herbicides include diflufenican, mefenacet and monalide. Diflufenican is particularly preferred.

In a yet further aspect, the present invention provides herbicidal compositions as defined above comprising a sulphonylurea derivative and a mixture of two or more of the above listed co-herbicides.

The compositions according to the invention may contain the sulfonylurea derivative and the co-herbicide in a wide range of ratios, depending on the particular conditions of application, the crop being treated, the weeds being combated and the type of herbicides being used in the compositions.

According to another embodiment of the present invention, advantageous combinations may comprise the sulfonylurea derivative (I) disclosed above and a mixture of two or more of the above-cited co-herbicides.

In a further aspect the present invention provides a process for selectively controlling the growth or germination of undesired plants comprising applying sequentially or simultaneously, pre- or post-emergent to the plants, to the seeds thereof, or to the locus of the seed or plants or seeds, the herbicidally active constituents of a composition according to the invention.

Thus it is to be understood that the present invention includes the application of the individual herbicidal constituents of the compositions of the present invention simultaneously or sequentially to the seed, plant or locus of the seed or plant. A simultaneous application is preferred. In this latter case, the composition may be applied:

(a) in the form of a tank mix of the individual herbicidal constituents, if desired complemented by the incorporation of agriculturally known adjuvants, such as cariers, diluents, surfactants, anti-freeze agents, and the like;

(b) in the form of a finely-divided powdered mixture of the sulfonylurea derivative and the co-herbicide;

(c) in the form of a ready-to-use formulated composition comprising the herbicidal components as defined complemented by formulation aids, surfactants, etc; or (d) in the form of a solution, dispersion or emulsion of a more concentrated, or even solid, formulated product which again comprises the herbicidal constituents, formulation aids and other agriculturally known adjuvants.

The application rates of the compositions of the invention depend upon the particular conditions of use and on the particular herbicidal composition being applied.

Herbicidal compositions containing the sulfonylurea derivative and the co-herbicide as well as formulations derived thereof, including concentrates of aqueous or non-aqueous solutions and of aqueous suspensions which require dilution prior to application, are all embodiments of the present invention and are all referred to hereafter by the term compositions. The compositions may contain the herbicidally active components mixture in a range from 0.1% to 100% weight and may also contain at least one agriculturally acceptable adjuvant in liquid or solid form. In the compositions the herbicidal components may be present in free form or in the form of an agriculturally acceptable acid addition salt, complex or association product, such as for example a complex or association product formed with metal ions.

The compositions are prepared by known techniques by ad-mixing the herbicidally active ingredients with one or more adjuvants, including diluents, extenders, carriers and conditioning agents, to provide compositions in the form of finely divided particulate solids, granules, pellets, solutions, dispersions or emulsions. Thus the active ingredients can be used with an adjuvant such as a finely divided solid, a liquid of organic origin, water, a surfactant, a dispersing agent, an emulsifying agent, a stabilising agent, an anti-freeze agent, an anti-foam agent or any suitable combination of these.

Suitable solvents include water, alcohols (e.g. methanol, ethanol, n-propanol, isopropanol, ethylene glycol, etc.), ketones (e.g. acetone, methyl ethyl ketone, etc.) ethers (e.g. dioxane, tetrahydrofuran, ethylene glycol monomethyl ether, diethylene glycol monomethyl ether, propylene glycol monomethyl ether, etc.), aliphatic hydrocarbons (e.g. kerosene, lamp oil, fuel oil, machine oil, etc.), aromatic hydrocarbons (e.g. benzene, toluene, xylene, solvent naphta, methylnaphthalene, etc.) halogenated hydrocarbons (e.g. dichloromethane, chloroform, carbon tetrachloride, etc.), acid amides (e.g. dimethylformamide, dimethylacetamide, etc.), esters (e.g. ethyl acetate, butyl acetate, fatty acid glycerol ester, etc.) and nitriles (e.g. acetonitrile, propionitrile, etc.). These solvents may be used individually or in a suitable mixed form of two or more ingredients in a suitable ratio.

Examples of the solid carrier (diluent/extender) include vegetable powders (e.g. soybean meal; tobacco powder, wheat flour, sawdust, etc.), mineral powders (e.g. clays such as kaolin, bentonite, terra alba, talcs such as talcum powder and agalmotalite powder, and silicas such as diatomaceous earth and mica powder), alumina, sulfur powder, and active carbon. These solid carriers may be used individually or in a suitable mixed form or two or more ingredients in a suitable ratio.

The above-mentioned liquid or solid vehicles (or carriers) can be used independently or in combination. An amount of the vehicle is in the range of up to 100% by weight of the whole composition.

Suitable surfactants include alkyl benzene sulfonates and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkyl arylethers, polyoxyethylene derivatives of alkylphenols (particularly isooctylphenol and nonylphenol) and polycxyethylene derivatives of the mono-higher fatty acid esters of hexitol anhydrides (e.g., sorbitan), polyoxyethylene allyl phenyl ether formaldehyde condensates, polyoxyethylene phenyl phenol ether sulfates, polyoxyethylene aryl ethers, alkoxylated amines, inorganic ammonium salts, such as ammonium sulphate, ammonium nitrate and ammonium phosphates, ammonium salts derived from organic amines such as primary, secondary and tertiary amines, diamines such as ethylene diamine and piperazine, morpholine, polyamines, alkoxylated amines and amine surfactants. Preferred dispersants are methylcellulose, polyvinyl alcohol, sodium lignin sulfonates, polymeric alkyl naphthalene sulfonates, sodium naphthalene sulfonate, and polymethylene bisnaphthalene sulfonate.

Wettable powders are water-dispersible compositions containing the active ingredients mixture, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably 5 to 20 parts) of active ingredients mixture, from about 0.25 to 25 parts (preferably 1 to 15 parts) of wetting agent, from about 0.25 to about 25 parts (preferably 1 to 15 parts) of dispersant and from 5 to about 95 parts (preferably 5 to 50 parts) of inert solid extender, all parts being by weight of the total composition. Where required, from about 0.1 to 2.0 parts of the solid inert extender can be replaced by a corrosion inhibitor or anti-foaming agent or both.

The compositions of the invention may be in the form of water dispersible granules (WG) comprising the herbicidally-active constituents together with surfactants, dispersing agents, disintegrating agents, fillers, diluents and the like.

The compositions may also be formulated as dust concentrates comprising from 0.1 to 60% by weight of the active ingredients in admixture with a suitable extender or diluent; these dusts may be diluted for application at concentrations within the range of about 0.1 to about 10% weight.

Compositions which are aqueous suspensions or emulsions may be prepared by stirring a non-aqueous solution of a water insoluble active ingredients mixture and an emulsification agent with water until uniform and then homogenizing to give an emulsion of very finely divided particles. The resulting concentrated aqueous suspension is characterized by its extremely small particle size so that when diluted and sprayed, coverage is very uniform. Suitable concentrations of these formulations contain from about 0.1 to 60%, preferably 5 to 50%, by weight of active ingredients mixture, the upper limit being determined by the solubility limit of active ingredients in the solvent.

Concentrates are usually solutions of active ingredients mixtures in water-immiscible, partially water-miscible or water-miscible solvents together with a surface active agent. Suitable solvents for the active ingredients of this invention include dimethylformamide, dimethylsulfoxide, N-methylpyrrolidone, hydrocarbons, amines and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain about 0.1 to 95 parts (preferably 5 to 60 parts) active ingredients mixture, about 0.25 to 50 parts (preferably 1 to 25 parts) surface active agent and where required about 4 to 94 parts solvent, all parts being by weight based on the total weight of emulsifiable oil.

The compositions of the invention can also be in the form of granules which are physically stable particulate compositions comprising active ingredient mixtures adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite, and vermiculite are examples of operable classes of particulate mineral extenders. The preferred extenders are the porous, absorptive, preformed particules such as preformed and screened particulate attapulgite or heat expanded, particulate vermiculite and the finely divided clays such as kaolin clays, hydrated attapulgite or bentonitic clays. These extenders are sprayed or blended with the active ingredient to form the herbicidal granules.

The granular compositions of this invention may contain from about 0.1 to 30 parts by weight of active ingredients mixture per 100 parts by weight of clay and 0 to about 5 parts by weight of surface active agent per 100 parts by weight of particulate clay.

The compositions of this invention can also contain other additives for example, fertilizers, other herbicides, other pesticides, safeners and other additives commonly used in herbicidal formulations, used as adjuvants or in combination with any of the above-described adjuvants.

Suitable surfactants may be found in "Mc. Cutcheon's Detergents and Emulsifiers Annual", Mc Publishing Corp., Ridgewood, N.J. or in equivalent technical documents.

It is generally admitted that, in case of synergism, the effectiveness of the mixture cannot be computed from that of the individual ingredients. Synergism is generally defined as the simultaneous action of two or more compounds in which the total response of an organism to the pesticide combination is greater that the sum of the individual components.

A simple mathematical method to test the additivity of a pesticide combination is based on the equation:

$$E = X + \frac{Y(100 - X)}{100}$$

in which X and Y represent the percentage-of-inhibition of growth by toxicant A and B, respectively. E is the expected percentage-of-inhibition of growth by the mixture A and B. In order to show synergism, the actual efficacy should be higher than E.

The compositions of the invention are active against a variety of weeds and are particularly useful for combating weeds which tend to infest cereal crops, for example the weeds which are listed above on page 2 of this specification. Other weeds combated by the herbicidal compositions of the present invention include, for example, the following:

| | |
|---|---|
| Amaranthus retroflexus | (pigweed) |
| Abutilon theophrasti | (velvet leaf) |
| Sida spinosa | (prickly sida) |
| Sesbania exaltata | (hemp sesbania) |
| Xanthium pennsylvanicum | (cockleburr) |
| Bidens spp. | (marigold) |
| Convolvulus arvensis | (field bindweed) |
| Papaver rhoeas | (field poppy) |
| Chrysanthemum segetum | (corn marigold) |
| Digitaria sanguinalis | (crabgrass) |
| Setaria faberii | (giant foxtail) |
| Solanum nigrum | (black nightshade) |
| Cyperus esculentus | (edible cyperus) |
| Echinochloa crus-galli | (barnyard grass) |
| Avena fatua | (wild oat) |
| Avena sterilis | (animated oat) |
| Lolium multiflorum | (rye grass) |
| Agropyron repens | (quack grass) |
| Plantago major | (greater plantain) |
| Cyodon cactylon | (bermuda grass) |
| Spergula arvensis | (corn spurrey) |
| Sinapsis arvensis | (wild mustard) |
| Ipomea purpurea | (morning glory) |
| Chenopodium album | (fat hen) |
| Ranunculus avensis | (corn butter cup) |
| Rubus fructicosus | (blackberry) |
| Portulaca oleracea | (purslane) |
| Polygonum convolvulus | (wild buckwheat) |
| Brassica synapsis | (yellow charlock) |
| Achillia milleflorum | (yarrow) |

Other species of weeds which are combated, variously, by the compositions of the present invention, depending upon the chosen sulfonylurea and the particular co-herbicide(s) combination include the following: Senecio, Vicia, Ambrosia, Anthemis, Sorghum, Aristolochia, Agrostis, Bromus, Tussilago, Carsium, Viola, Atriplex, Apera, Poa, Capsella, Galinsoga, Datura, Euphorbia, Taraxacum, Plantago, Cynodon, Rumex, and Oxalis.

The invention is illustrated by the following Examples.

EXAMPLE 1

Two sulfonylurea compounds A and B having the structural formulae shown below:

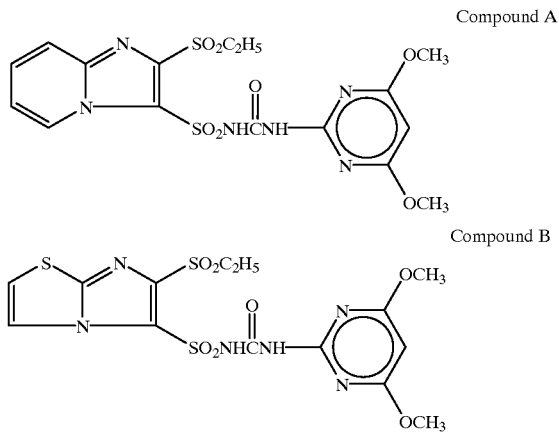

are formulated as suspension concentrates (SC) containing about 42% by weight of active ingredient.

The compounds were tested alone and in admixture with a co-herbicide, which was also tested alone, against the following weeds:

| Weed | Designation |
|---|---|
| *Alopecurus myosuroides* (black grass) | ALOMY |
| *Avena fatua* (wild oats) | AVENA |
| *Galium aparine* (bedstraw cleavers) | GALAP |
| *Lamium purpureum* (red dead nettle) | LAMPU |
| *Matricaria chamomilla* (mayweed) | MATCH |
| *Stellaria media* (common chickweed) | STEME |
| *Veronica persica* (common field speedwell) | VERPE |

In the test procedure three replicate pots per treatment were randomly arranged through a growth room. The plants were treated about three weeks after planting and then submitted to a photoperiod of 14 hours per day; the temperature was 15 degrees Centigrade during the day and 9 degrees at night. All applications of test formulations were performed using a MARDRIVE sprayer, simulating as far as possible field conditions. The pressure was controlled at 2 bar and the water volume was 300 l/ha. The weed plants were at a true leaf stage between 0 to 6 leaves.

Assessment of phytotoxicity was made by comparison with untreated control pots on an arbitrary scale from 0 to 100%, where 0 represents no visible effect and 100 represents a kill of all plants. The results in the tables and figures are presented as average values of three replicates.

The co-herbicides tested were, variously, isoproturon (IPU) (urea herbicide), imazamethabenz-methyl (imidazolinone herbicide), bifenox (diphenyl ether herbicide), bromoxynil (hydroxybenzonitrile herbicide), triallate (carbamate herbicide), difenzoquat (quaternary ammonium salt), flupoxam (triazole herbicide), MCPP (phytohormone herbicide), pendimethalin (2,6-dinitroaniline herbicide), fluroxypyr (phytohormone herbicide), fenoxaprop-P-ethyl (2-(4-aryloxyphenoxy) alkanoic acid herbicide), isoxaben (amide herbicide) and diflufenican (anilide herbicide). Fenoxaprop-P-ethyl has been used as the commercial product PUMA® which contains a safener. The safener is believed to reduce the injury to wheat caused by fenoxaprop-P-ethyl in order to render same commercially more vialable in the competitive environment.

The results of the tests are presented in Table I below.

The results of the tests demonstrate the synergistic effects possessed by the compositions of the invention. Turning again to fenoxaprop-P-ethyl, it should be noticed that the activity on the weeds has been synergized while maintaining the safety of the fenoxaprop-P-ethyl/safener combination to the crop. In practice, this could lead to a reduced use of safener.

TABLE I

Synergy between Sulfonylurea Compounds A and B and various Co-herbicides

| Weed | Rate (g/ha.) SU + X | SU − A | X | Ex | Obs | SU − B | X | Ex | Obs |
|---|---|---|---|---|---|---|---|---|---|
| *Isoproturon* | | | | | | | | | |
| ALOMY | 20 + 1000 | 0 | 0 | 0 | 80 | 10 | 0 | 10 | 70 |
| AVEFA | 30 + 1000 | 0 | 0 | 0 | 40 | 0 | 0 | 0 | 10 |
| GALAP | 20 + 500 | 60 | 0 | 60 | 90 | 80 | 0 | 80 | 95 |
| LAMPU | 20 + 500 | 0 | 25 | 25 | 30 | 0 | 25 | 25 | 40 |
| STEME | 20 + 500 | 60 | 0 | 60 | 90 | 20 | 0 | 20 | 80 |
| VERPE | 20 + 500 | 70 | 0 | 70 | 85 | 50 | 0 | 50 | 80 |
| *Imazamethabenz* | | | | | | | | | |
| ALOMY | 10 + 300 | 10 | 15 | 23.50 | 85 | 10 | 15 | 23.50 | 70 |
| AVEFA | 20 + 100 | 10 | 30 | 37 | 60 | 0 | 30 | 30 | 55 |
| LAMPU | 10 + 300 | 70 | 60 | 88 | 97 | — | — | — | — |
| MATCH | 20 + 300 | 90 | 5 | 90.50 | 97 | 60 | 5 | 62 | 95 |
| STEME | 10 + 100 | 70 | 10 | 73 | 90 | 50 | 10 | 55 | 60 |
| VERPE | 10 + 300 | 30 | 10 | 37 | 95 | 85 | 10 | 86.50 | 95 |
| VERPE | 20 + 200 | 50 | 0 | 50 | 90 | — | — | — | — |
| *Difenzoquat* | | | | | | | | | |
| ALOMY | 30 + 600 | 25 | 5 | 28.5 | 80 | — | — | — | — |
| AVEFA | 10 + 600 | 0 | 60 | 60 | 75 | — | — | — | — |
| LAMPU | 10 + 600 | 30 | 5 | 33.50 | 90 | — | — | — | — |
| STEME | 10 + 400 | 50 | 0 | 50 | 95 | — | — | — | — |
| VERPE | 20 + 200 | 50 | 0 | 50 | 90 | — | — | — | — |
| *Triallate* | | | | | | | | | |
| ALOMY | 10 + 1500 | 10 | 50 | 55 | 80 | 25 | 50 | 62.50 | 80 |
| AVEFA | 20 + 1500 | 15 | 65 | 70.25 | 75 | 5 | 65 | 66.75 | — |
| LAMPU | 20 + 1500 | — | — | — | — | 20 | 50 | 60 | 85 |
| MATCH | 20 + 1500 | 45 | 10 | 50.50 | 80 | — | — | — | — |
| STEME | 30 + 1000 | 65 | 10 | 68.50 | 75 | — | — | — | — |
| VERPE | 20 + 500 | — | — | — | — | 50 | 40 | 70 | 80 |
| *Difenzoquat* | | | | | | | | | |
| ALOMY | 30 + 600 | 25 | 5 | 28.5 | 80 | — | — | — | — |
| AVEFA | 10 + 600 | 0 | 60 | 60 | 75 | — | — | — | — |
| LAMPU | 10 + 600 | 30 | 5 | 33.50 | 90 | — | — | — | — |
| STEME | 10 + 400 | 50 | 0 | 50 | 95 | — | — | — | — |
| VERPE | 20 + 200 | 50 | 0 | 50 | 90 | — | — | — | — |
| *MCPP* | | | | | | | | | |

TABLE I-continued

Synergy between Sulfonylurea Compounds A and B and various Co-herbicides

| Weed | Rate (g/ha.) SU + X | SU – A | X | Ex | Obs | SU – B | X | Ex | Obs |
|---|---|---|---|---|---|---|---|---|---|
| ALOMY | 10 + 1000 | 0 | 0 | 0 | 60 | 0 | 0 | 0 | 65 |
| AVEFA | 20 + 1000 | 0 | 0 | 0 | 20 | 0 | 0 | 0 | 10 |
| MATCH | 10 + 250 | 70 | 30 | 79 | 95 | 70 | 30 | 79 | 90 |
| STEME | 10 + 250 | 50 | 85 | 92.50 | 100 | 0 | 85 | 85 | 99 |
| Pendimethalin ||||||||||
| ALOMY | 30 + 800 | 10 | 10 | 19 | 65 | 20 | 10 | 28 | 75 |
| AVEFA | 30 + 1200 | 0 | 0 | 0 | 70 | 0 | 0 | 0 | 60 |
| GALAP | 10 + 1200 | 60 | 60 | 84 | 90 | 70 | 60 | 88 | 95 |
| LAMPU | 10 + 400 | 0 | 70 | 70 | 80 | 0 | 70 | 70 | 80 |
| MATCH | 30 + 800 | 70 | 50 | 85 | 97 | 90 | 50 | 95 | 97 |
| STEME | 30 + 800 | 55 | 0 | 55 | 95 | 30 | 0 | 30 | 90 |
| VERPE | 20 + 1200 | 70 | 90 | 97 | 99 | 50 | 90 | 95 | 99 |
| Fluroxypyr ||||||||||
| ALOMY | 30 + 100 | 20 | 0 | 20 | 75 | 40 | 0 | 40 | 70 |
| AVEFA | 30 + 100 | 10 | 0 | 10 | 65 | 0 | 0 | 0 | 10 |
| GALAP | 10 + 50 | 20 | 70 | 76 | 90 | 0 | 70 | 70 | 95 |
| LAMPU | 20 + 1000 | 30 | 50 | 65 | 85 | 10 | 50 | 55 | 75 |
| MATCH | 10 + 100 | 40 | 20 | 52 | 99 | 10 | 20 | 28 | 50 |
| STEME | 10 + 100 | — | — | — | — | 0 | 60 | 60 | 80 |
| VERPE | 10 + 100 | 20 | 85 | 88 | 95 | 10 | 85 | 86.50 | 99 |
| Flupoxam ||||||||||
| ALOMY | 20 + 100 | — | — | 30 | 60 | — | — | — | — |
| AVEFA | 20 + 100 | — | — | 10 | 30 | — | — | 0 | 10 |
| Bifenox ||||||||||
| ALOMY | 10 + 500 | — | — | 20 | 35 | — | — | 25 | 35 |
| AVEFA | 30 + 1000 | — | — | 28 | 55 | — | — | 10 | 25 |
| Bromoxynil ||||||||||
| ALOMY | 30 + 1000 | — | — | 30 | 40 | — | — | 40 | 50 |
| AVEFA | 30 + 1000 | — | — | 10 | 35 | — | — | 0 | 20 |
| Fenoxaprop-P-ethyl ||||||||||
| ALOMY | 30 + 60 | — | — | 55 | 75 | — | — | 65 | 90 |
| AVEFA | 30 + 30 | — | — | 19.25 | 45 | — | — | 9.80 | 20 |
| Isoxaben ||||||||||
| ALOMY | 10 + 60 | — | — | 35 | 55 | — | — | 45 | 60 |
| AVEFA | 30 + 60 | — | — | 30 | 45 | — | — | 20 | 30 |
| Diflufenican ||||||||||
| ALOMY | 10 + 150 | — | — | 19 | 30 | — | — | 32.50 | 40 |
| AVEFA | 30 + 150 | — | — | 28.75 | 35 | — | — | 14.50 | 20 |

Key to Table I

IPU=Isoproturon

SU=Sulfonylurea

Key to Table I (continued)

SU—A=Sulfonylurea Compound A IPU=Isoproturon

SU—B=Sulfonylurea Compound B

Ex=Expected

Obs=Observed

X=coherbicide as specified at the top of each individual table

What is claimed is:

1. A herbicidal composition comprising a sulfonylurea derivative of formula

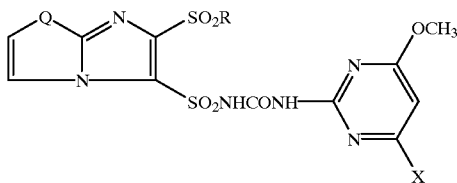

wherein Q is —CH=CH— or —S—, R is straight or branched C1–3 alkyl, and X is —OCH$_3$ or —CH$_3$, or an agriculturally acceptable salt thereof, and at least one co-herbicide from the following herbicides:
isoproturon, a urea herbicide,
imazamethabenz-methyl, an imidazolinone,
bifenox, a diphenyl ether herbicide,
bromoxynil, a hydroxybenzonitrile herbicide,
fenoxaprop-P-ethyl, a 2-(4-aryloxyphenoxy) alkanoic acid herbicide,
tri-allate, a carbamate/thiocarbamate herbicide, difenzoquat metilsulfate, a quaternary ammonium salt herbicide,
MCPP and fluroxpyr, phytohormone herbicides,
pendimethalin, a 2,6-dinitroaniline herbicide,
isoxaben, an amide herbicide,
diflufenican, an anilide herbicide;
the respective herbicidal constituents being present in amounts whereby the compositions display selectivity of herbicidal action with respect to crops being treated pre- or post-emergent and exhibit synergistic effects when applied at herbicidally effective rates.

2. A herbicidal composition according to claim 1 wherein the agriculturally acceptable salt is a salt formed with an inorganic base selected from the group consisting of alkali metals, alkali earth metals, ammonia, and organic bases selected from the group consisting of dimethylamine, triethylamine, pyrrolidine, piperidine, piperazine, morpholine, benzylamine, ethanolamine, and diethanolamine.

3. A herbicidal composition as claimed in claim 1 or claim 2 wherein the sulphonylurea is a compound of formula:

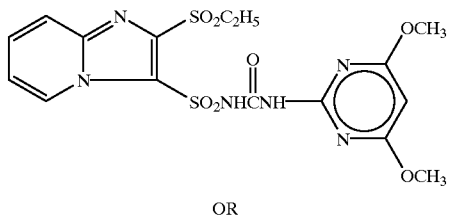

OR

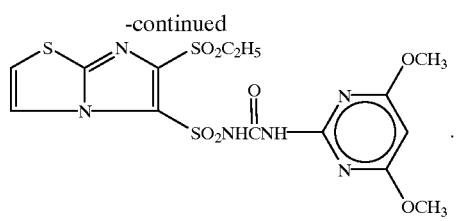

4. A herbicidal composition according to claim 1 wherein —R is —C2H5, —X is —OCH3 and Q is —CH=CH—.

5. A herbicidal composition according to claim 1 wherein the ratio by weight of the sulfonylurea herbicide to the co-herbicide is from about 1:1 to about 1:150 and the amounts applied are in the ratio of from about 10:30 g/ha to about 25:1500 g/ha.

6. A method of controlling the germination and growth of undesired vegetation in a selective manner with regard to crops being treated, which comprises applying to the crops, pre- or post-emergent, a composition as claimed in any one of claims 1, 2, 4 or 5.

7. A process for selectively controlling the growth or germination of undesired plants comprising applying sequentially or simultaneously, pre- or post-emergent to the plants, to the seeds thereof, or to the locus of the seed or plants or seeds, the herbicidally active constituents of a composition as claimed in any one of claims 1, 2, 4 or 5.

* * * * *